United States Patent
Shih et al.

(10) Patent No.: US 9,346,719 B2
(45) Date of Patent: May 24, 2016

(54) CATALYST SYSTEMS AND SELECTIVE HYDROGENATION PROCESSES

(75) Inventors: Kuo-Chen Shih, Kaohsiung (TW); Hung-Yu Chen, Tainan (TW); Mao-Lin Hsueh, Pingtung County (TW); Yi-Zhen Chen, Yilan County (TW)

(73) Assignees: INDUSTRIAL TECHNOLOGY RESEARCH INSTITUTE, Hsinchu (TW); LEE CHANG YUNG CHEMICAL INDUSTRY CORPORATION, Taipei (TW)

( * ) Notice: Subject to any disclaimer, the term of this patent is extended or adjusted under 35 U.S.C. 154(b) by 1360 days.

(21) Appl. No.: 12/842,240

(22) Filed: Jul. 23, 2010

(65) Prior Publication Data

US 2011/0021852 A1 Jan. 27, 2011

(30) Foreign Application Priority Data

Jul. 24, 2009 (TW) .............................. 98124977 A

(51) Int. Cl.
*C07C 5/10* (2006.01)
*B01J 31/12* (2006.01)
*C07C 5/03* (2006.01)
*B01J 31/22* (2006.01)

(52) U.S. Cl.
CPC ............... *C07C 5/03* (2013.01); *B01J 31/122* (2013.01); *B01J 31/2295* (2013.01); *B01J 2231/645* (2013.01); *B01J 2531/46* (2013.01); *C07C 2101/16* (2013.01); *C07C 2102/08* (2013.01); *C07C 2102/10* (2013.01); *C07C 2103/18* (2013.01); *C07C 2531/12* (2013.01); *C07C 2531/38* (2013.01); *Y02P 20/52* (2015.11)

(58) Field of Classification Search
None
See application file for complete search history.

(56) References Cited

U.S. PATENT DOCUMENTS

| 3,541,064 A | 11/1970 | Yoshimoto et al. |
| 3,644,588 A | 2/1972 | Hassell |
| 3,700,633 A | 10/1972 | Wald et al. |
| 3,868,354 A | 2/1975 | Halasa |
| 5,948,869 A * | 9/1999 | Vallieri et al. ............... 525/338 |
| 5,994,477 A * | 11/1999 | Ko et al. ....................... 525/338 |
| 6,313,230 B1 | 11/2001 | Tsai et al. |

FOREIGN PATENT DOCUMENTS

| CN | 1177599 A | 4/1998 |
| CN | 1324867 A | 12/2001 |
| TW | 426689 B | 3/2001 |
| TW | I225493 B | 12/2004 |

OTHER PUBLICATIONS

Corresponding Chinese Office Action 200910173407.3, Issued on Dec. 31, 2011.
Taiwanese Office Action dated Dec. 22, 2012, for TW Application No. 98124977.

* cited by examiner

*Primary Examiner* — Yun Qian
(74) *Attorney, Agent, or Firm* — Birch, Stewart, Kolasch & Birch, LLP

(57) ABSTRACT

A hydrogenation catalyst system is provided. The catalyst system includes a metal complex of Formula (I), an organic lithium compound and an organic compound having a cyclic structure including at least one double bond.

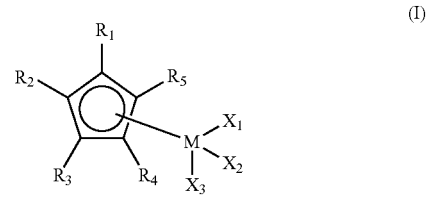

In Formula (I), M is transition metals. $R_1$, $R_2$, $R_3$, $R_4$ and $R_5$ are the same or different, including hydrogen, C1-8 alkyl, and C1-8 alkoxy, or two of $R_1$, $R_2$, $R_3$, $R_4$ and $R_5$ are linked together to form a ring. $X_1$, $X_2$ and $X_3$ are a cyclic group, hydrogen, chlorine, bromine, alkyl or alkoxy, wherein when one of $X_1$, $X_2$ and $X_3$ is a cyclic group, and the others are the same or different, including hydrogen, chlorine, bromine, alkyl or alkoxy. The invention also provides a selective hydrogenation process utilizing the catalyst system.

5 Claims, No Drawings

CATALYST SYSTEMS AND SELECTIVE HYDROGENATION PROCESSES

CROSS REFERENCE TO RELATED APPLICATIONS

This application claims priority of Taiwan Patent Application No. 98124977, filed on Jul. 24, 2009, the entirety of which is incorporated by reference herein.

BACKGROUND OF THE INVENTION

1. Field of the Invention

The invention relates to a catalyst system, and more particularly to a hydrogenation catalyst system and a selective hydrogenation process utilizing the same.

2. Description of the Related Art

A polymer of conjugated diene monomer such as 1,3-butadiene or isoprene, or a copolymer with a vinyl aromatic monomer such as styrene that may be copolymerized with the conjugated diene monomer, has been widely used as an elastomer in many fields. However, the weather resistance, thermal resistance, oxidation resistance and ozone resistance of such copolymers are apparently insufficient with the unsaturated carbon-carbon double bonds within the main chains, limiting the use range of the polymers.

In an effort to improve the durability and oxidation resistance of a polymer having unsaturated double bonds, a process for selectively hydrogenating the double bonds in the polymers may be generally adopted.

Various methods to hydrogenate polymers having olefinic unsaturated double bonds have been reported, and could be classified into two main catalogs. The first one is to use a heterogeneous catalyst, while the second one is to use a Ziegler catalyst or a homogeneous catalyst belonging to organometallic compounds such as cobalt or nickel or titanium.

A typical heterogeneous catalyst consists of a catalytically active ingredient and a support. The active ingredient, such as platinum and palladium, is impregnated into the support, such as carbon, silica and alumina. For the homogeneous catalyst system, an organometallic compound containing transition metal(s), such as nickel, cobalt and titanium, is mixed with an organometallic compound serving as a reductant, such as organo aluminum, organo magnesium and organo lithium. Compared to the heterogeneous catalysts, homogeneous catalysts are higher in hydrogenation activity and need a lower temperature and pressure for the catalytic reaction. In the case of polymers, the heterogeneous catalysts have more serious difficulty in hydrogenating them because of the high viscosity of the reaction system and the steric hindrance of the polymers, usually requiring severe reaction conditions. In particular, the selective hydrogenation of olefinic polymer in a copolymer containing conjugated diene monomer and vinyl aromatic monomer under such severe reaction conditions is extremely difficult, since the unsaturated double bonds of an aromatic compound could be simultaneously hydrogenated. Thus, the heterogeneous catalyst is economically unfavorable not only because a large quantity of the catalyst is required for effective hydrogenation, but also because of the high temperature and pressure causing the polymers to be decomposed and gelled.

In contrast, the homogeneous catalysts are very advantageous by virtue of high reactivity and hydrogenation efficiency even at a milder reaction such as a lower temperature and pressure.

Several methods to selectively hydrogenate the unsaturated double bonds of conjugated diene polymers have been disclosed as set forth hereunder. U.S. Pat. Nos. 3,644,588, 3,868,354, 3,541,064 and 3,700,633 disclose catalyst systems for hydrogenating or selectively hydrogenating ethylenically unsaturated polymers or ethylenically unsaturated aromatic copolymers, in which the metals of group VIII on the Periodic Table, especially, nickel or cobalt, are combined with the metals of groups IA, IIA and IIIB on the Periodic Table, especially, lithium, magnesium and aluminum alkyl as reductants. Such catalyst systems can effectively hydrogenate the unsaturated double bonds of the butadiene copolymer.

However, the above-described homogeneous catalysts have recognized some disadvantages in that a) since it is in general extremely sensitive to the outer circumstances, the catalyst may be easily decomposed in air, or in the presence of moisture, and b) the hydrogenation activity may greatly vary depending upon the reduction state of catalyst. In consequence, it is very difficult to satisfy the high degree of hydrogenation yield and reproducibility simultaneously. Such trend will badly affect the hydrogenation of a polymer designed to improve the durability and oxidation resistance of a polymer. Furthermore, the hydrogenation rate of the homogeneous catalyst is much affected depending on its stability during the hydrogenation.

Now that the industrial application of a homogeneous catalyst in the hydrogenation of polymer has faced the above problems, there are strong needs for the development of a highly active hydrogenation catalyst with better stability and reproducibility.

BRIEF SUMMARY OF THE INVENTION

To overcome the shortcomings in hydrogenating the unsaturated double bonds of a conjugated diene polymer when the homogeneous catalyst is used, an object of this invention is to provide a hydrogenation method using a novel catalyst system so as to prepare a hydrogenated polymer with a high degree of hydrogenation yield and reproducibility, without any drawbacks the existing homogeneous hydrogenation catalysts have encountered.

To achieve the above objective, this invention is characterized by a method for the selective hydrogenation of polymer containing conjugated diene in hydrogenating the double bonds only in the conjugated dienes of polymer, which is selected from a homopolymer of conjugated diene monomer or a copolymer consisting of a conjugated diene monomer and aromatic vinyl monomer, wherein the catalyst system comprises a metal complex of Formula (I), an organic lithium compound and an organic compound having a cyclic structure comprising at least one double bond.

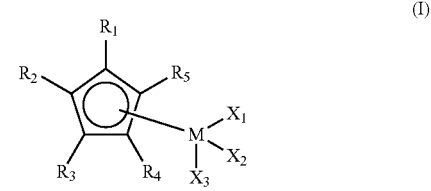

(I)

In Formula (I), M is a transition metal, selected from titanium, zirconium or hafnium. $R_1$, $R_2$, $R_3$, $R_4$ and $R_5$ are the same or different, comprising hydrogen, C1-8 alkyl, and C1-8 alkoxy, or two of $R_1$, $R_2$, $R_3$, $R_4$ and $R_5$ are linked together to form a ring. $X_1$, $X_2$ and $X_3$ are a cyclic group, hydrogen, chlorine, bromine, alkyl or alkoxy, wherein when one of $X_1$, $X_2$ and $X_3$ is a cyclic group, and the others are the same or different, comprising hydrogen, chlorine, bromine, alkyl or alkoxy. The organic lithium compound has a formula of LiR, wherein R is C1-6 alkyl. The organic compound having a cyclic structure containing at least one double bond is C3-18 hydrocarbons, preferably C5-14 hydrocarbons, comprising diphenylmethane, diphenylethane, dimethylbiphenyl, ethylbiphenyl, diphenylpropane, benzylbiphenyl, triphenylmethane, indene, methylindene, ethylindene, dihydronaphthalene, methylnaphthalene, ethylnaphthalene, fluorene, methylfluorene or ethylfluorene.

One embodiment of the invention provides a selective hydrogenation process comprising providing a polymer containing double bonds, and selectively hydrogenating the polymer containing double bonds in the presence of a catalyst system. The catalyst system comprises a metal complex of Formula (I), an organic lithium compound and an organic compound having a cyclic structure comprising at least one double bond.

The invention provides a catalyst system comprising a metal complex of Formula (I), an organic lithium compound and an organic compound having a cyclic structure containing at least one double bond to stabilize the high-activity catalyst system under moderate temperatures and hydrogen pressure.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a catalyst system comprising a metal complex of Formula (I), an organic lithium compound and an organic compound having a cyclic structure comprising at least one double bond.

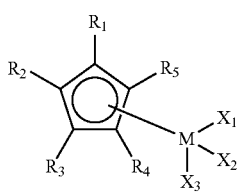

(I)

In Formula (I), M may be transition metals, for example titanium, zirconium or hafnium. $R_1$, $R_2$, $R_3$, $R_4$ and $R_5$ may be the same or different, for example hydrogen, C1-8 alkyl, and C1-8 alkoxy, or two of $R_1$, $R_2$, $R_3$, $R_4$ and $R_5$ may be linked together to form a ring. $X_1$, $X_2$ and $X_3$ may be a cyclic group such as cyclopentadiene, hydrogen, chlorine, bromine, alkyl or alkoxy. Specifically, when one of $X_1$, $X_2$ and $X_3$ is a cyclic group, and the others may be the same or different, for example hydrogen, chlorine, bromine, alkyl or alkoxy.

The organic lithium compound has a formula of LiR. R may be C1-6 alkyl. The organic compound having a cyclic structure containing at least one double bond may be C3-18 hydrocarbons, preferably C5-14 hydrocarbons, for example diphenylmethane, diphenylethane, dimethylbiphenyl, ethylbiphenyl, diphenylpropane, benzylbiphenyl, triphenylmethane, indene, methylindene, ethylindene, dihydronaphthalene, methylnaphthalene, ethylnaphthalene, fluorene, methylfluorene or ethylfluorene.

In the catalyst system, the metal complex and the organic compound having a cyclic structure containing at least one double bond have a molar ratio of about 0.1:1-50:1. Further, lithium and the metal complex have a preferable molar ratio of about 1:1-12:1. The organic compound having a cyclic structure containing at least one double bond and the organic lithium compound have a preferable molar ratio of 0.1:1-12:1.

One embodiment of the invention provides a selective hydrogenation process, comprising the following steps. A polymer containing double bonds is provided. Next, the double bonds are selectively hydrogenated in the presence of the catalyst system.

The catalyst system comprises a metal complex of Formula (I), an organic lithium compound and an organic compound having a cyclic structure comprising at least one double bond.

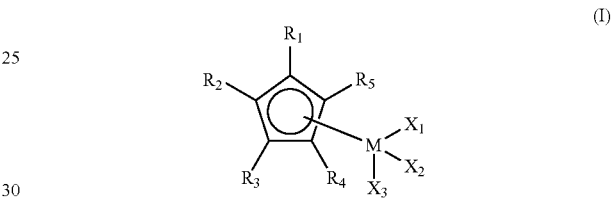

(I)

In Formula (I), M is a transition metal, for example titanium, zirconium or hafnium. $R_1$, $R_2$, $R_3$, $R_4$ and $R_5$ may be the same or different, for example hydrogen, C1-8 alkyl, and C1-8 alkoxy, or two of $R_1$, $R_2$, $R_3$, $R_4$ and $R_5$ may be linked together to form a ring. $X_1$, $X_2$ and $X_3$ may be a cyclic group such as cyclopentadiene, hydrogen, chlorine, bromine, alkyl or alkoxy. Specifically, when one of $X_1$, $X_2$ and $X_3$ is a cyclic group, and the others may be the same or different, for example hydrogen, chlorine, bromine, alkyl or alkoxy.

The organic lithium compound has a formula of LiR. R may be C1-6 alkyl. The organic compound having a cyclic structure containing at least one double bond may be C3-18 hydrocarbons, preferably C5-14 hydrocarbons, for example diphenylmethane, diphenylethane, dimethylbiphenyl, ethylbiphenyl, diphenylpropane, benzylbiphenyl, triphenylmethane, indene, methylindene, ethylindene, dihydronaphthalene, methylnaphthalene, ethylnaphthalene, fluorene, methylfluorene or ethylfluorene.

In the catalyst system, the metal complex and the organic compound having a cyclic structure containing at least one double bond have a molar ratio of about 0.1:1-50:1. Further, lithium and the metal complex have a preferable molar ratio of about 1:1-12:1. The organic compound having a cyclic structure containing at least one double bond and the organic lithium compound have a preferable molar ratio of 0.1:1-12:1.

The selective hydrogenation process is conducted under a temperature of 30-200° C., preferably 40-100° C., and a hydrogen pressure of 0.5-100 atm, preferably 2-20 atm.

The invention provides a modified co-catalyst, comprising an organic lithium compound and an organic compound having a cyclic structure containing at least one double bond to stabilize the high-activity catalyst system under moderate temperatures and hydrogen pressure.

Example 1

Preparation of a Styrene-Butadiene-Styrene (SBS) Polymer

An autoclave (2 L) was degassed and filled with a nitrogen atmosphere. Cyclohexane (910 g), tetrahydrofuran (2.2 g), and styrene (24 g) was then added to the autoclave, respectively. After butyl lithium (1.6M in hexane; 3 mL) was introduced, the autoclave was heated to 45° C., and the solution was stirred at a speed of 700 rpm for 30 minutes. The color of the solution turned to be orange-red. Butadiene (112 g) was then added to the solution, and the solution was under vigorously stirred for another one hour. The color of the solution changed to be a yellow color. Afterwards, styrene (24 g) was added to the solution and stirred for another one hour. The color of the solution returned to be an orange-red color, forming a styrene-butadiene-styrene (SBS) polymer.

The products resulting from the selective hydrogenation of the styrene-butadiene-styrene (SBS) polymers are analyzed by $^1$H-NMR spectroscopy to determine the degree of hydrogenation of the polymers. In the usual $^1$H-NMR analysis, the vinyl bonds will show a peak with the chemical shift at between 4.9 and 5.0 ppm. The 1,4-double bonds show two peaks with the chemical shifts, namely between 5.3 and 5.5 ppm and between 5.5 and 5.6 ppm. The degree of hydrogenation of the polymers was calculated from the ratio of the integrals of these olefinic protons.

Example 2

Under a nitrogen atmosphere, a SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of fluorene and butyl lithium in cyclohexane (fluorene/Li/Ti molar ratio: 3/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 3

Under a nitrogen atmosphere, a SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of fluorene and butyl lithium in cyclohexane (fluorene/Li/Ti molar ratio: 6/6/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 4

Under a nitrogen atmosphere, a SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of fluorene and butyl lithium in cyclohexane (fluorene/Li/Ti molar ratio: 1/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 5

The same equivalent of t-butyl chloride was added to a SBS solution (15 wt % in cyclohexane; 100 g; orange-red) and stirred until the color of the solution was changed from orange-red to colorless. The resulting SBS solution was added to an autoclave (250 mL) under a nitrogen atmosphere, followed by heating to 60° C., and pressured with hydrogen to 6 atm. A toluene (4 ml) solution of CpTiCl$_3$ (0.02 mmole/g polymer) was added thereto, followed by the addition of fluorene and butyl lithium in cyclohexane (fluorene/Li/Ti molar ratio: 6/6/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 6

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of indene and butyl lithium in cyclohexane (indene/Li/Ti molar ratio: 3/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 7

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of indene and butyl lithium in cyclohexane (indene/Li/Ti molar ratio: 1/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 8

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of indene and butyl lithium in cyclohexane (indene/Li/Ti molar ratio: 6/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 9

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of 1,2-dihydronaphthalene and butyl lithium in cyclohexane (1,2-dihydronaphthalene/Li/Ti molar ratio: 3/3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Comparative Example 1

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto, followed by the addition of toluene and butyl lithium in cyclohexane (UM molar ratio: 3/1). The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Comparative Example 2

Under a nitrogen atmosphere, the SBS solution (15 wt % in cyclohexane; 100 g) was added to an autoclave (250 mL), followed by heating to 60° C., and pressured with hydrogen to 6 atm. A toluene (4 ml) solution of CpTiCl$_3$ (0.02 mmole/g polymer) was added thereto. The hydrogen pressure inside the autoclave was increased to 10 atm, and the solution was under vigorously stirred at 60° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Example 10

Under a nitrogen atmosphere, the SBS solution (15 wt % in cyclohexane; 100 g) was added to an autoclave (250 mL), followed by heating to 50° C. A toluene (15 ml) solution of Cp$_2$TiCl$_2$ (0.0182 mmole/g polymer) and indene and butyl lithium in cyclohexane (indene/Li/Ti molar ratio: 4/5/1) was added thereto. The hydrogen pressure inside the autoclave was increased to 5 atm, and the solution was under vigorously stirred at 50° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

Comparative Example 3

Under a nitrogen atmosphere, the SBS solution (15 wt % in cyclohexane; 100 g) was added to an autoclave (250 mL), followed by heating to 50° C. A toluene (15 ml) solution of Cp$_2$TiCl$_2$ (0.0182 mmole/g polymer) and butyl lithium in cyclohexane (Li/Ti molar ratio: 4/1) was added thereto. The hydrogen pressure inside the autoclave was increased to 5 atm, and the solution was under vigorously stirred at 50° C. for 4 hours. The autoclave was then cooled to room temperature, and the inside pressure was lowered to the atmospheric pressure, followed by replacing with a nitrogen atmosphere. The reaction mixture was added to methanol to precipitate out the polymer. The polymer was then dried at a temperature of about 60° C. for 12 hours. The degree of hydrogenation of the polymer was determined by a $^1$HNMR, and was shown in Table 1.

TABLE 1

|  |  | The hydrogenation degree (%) of SBS polymer | | |
| --- | --- | --- | --- | --- |
| Examples | Catalyst system (molar ratio) | The hydrogenation degree (%) of 1,4-double bond unit | The hydrogenation degree (%) of 1,2-vinyl bond unit | Total hydrogenation degree (%) |
| Example 2 | fluorene/BuLi/CpTiCl$_3$ = 3/3/1 | 93.6 | 100 | 95.1 |
| Example 3 | fluorene/BuLi/CpTiCl$_3$ = 6/6/1 | 25.2 | 81.7 | 37.7 |
| Example 4 | fluorene/BuLi/CpTiCl$_3$ = 1/3/1 | 100 | 100 | 100 |
| Example 5 | fluorene/BuLi/CpTiCl$_3$ = 3/3/1 | 95.9 | 96.9 | 96.1 |
| Example 6 | indene/BuLi/CpTiCl$_3$ = 3/3/1 | 99.7 | 100 | 99.8 |
| Example 7 | indene/BuLi/CpTiCl$_3$ = 1/3/1 | 99.7 | 99.4 | 99.6 |
| Example 8 | indene/BuLi/CpTiCl$_3$ = 6/3/1 | 99.7 | 98.2 | 99.4 |
| Example 9 | dihydronaphthalene/BuLi/CpTiCl$_3$ = 3/3/1 | 96.3 | 100 | 97.2 |
| Comparative Example 1 | BuLi/CpTiCl$_3$ = 3/1 | 38.0 | 86.5 | 49.9 |
| Comparative Example 2 | CpTiCl$_3$ | 6.7 | 4.3 | 6.2 |
| Example 10 | indene/BuLi/Cp$_2$TiCl$_2$ = 4/4/1 | 90.0 | 100 | 92.3 |
| Comparative Example 3 | BuLi/Cp$_2$TiCl$_2$ = 4/1 | 13.1 | 54.0 | 22.5 |

The results in Table 1 indicated that using the CpTiCl$_3$ and butyl lithium catalyst system with an additive of indene, fluorene or 1,2-dihydronaphthalene (Examples 2, 4, 5, 6, 7, 8 and 9) in a selective hydrogenation process, achieves a higher degree of hydrogenation than those of Comparative Examples 1 and 2. Additionally, using the Cp$_2$TiCl$_2$ catalyst system with an additive of indene (Example 10) also achieves a higher degree of hydrogenation than that of Comparative Example 3.

While the invention has been described by examples and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A catalyst system, comprising:
    a metal complex of Formula (I):

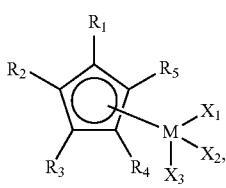

(I)

wherein M is a transition metal, $R_1$, $R_2$, $R_3$, $R_4$ and $R_5$ are the same or different, comprising hydrogen, C1-8 alkyl, and C1-8 alkoxy, or two of $R_1$, $R_2$, $R_3$, $R_4$ and $R_5$ are linked together to form a ring, and $X_1$, $X_2$ and $X_3$ are a cyclic group, hydrogen, chlorine, bromine, alkyl or alkoxy, wherein when one of $X_1$, $X_2$ and $X_3$ is a cyclic group, and the others are the same or different, comprising hydrogen, chlorine, bromine, alkyl or alkoxy;
    an organic lithium compound of a formula of LiR, wherein R is C1-6 alkyl; and
    an organic compound having a cyclic structure comprising at least one double bond comprising diphenylmethane, diphenylethane, dimethylbiphenyl, ethylbiphenyl, diphenylpropane, benzylbiphenyl, triphenylmethane, indene, methylindene, ethylindene, dihydronaphthalene, methylnaphthalene, ethylnaphthalene, fluorene, methylfluorene or ethylfluorene.

2. The catalyst system as claimed in claim 1, wherein M is titanium, zirconium or hafnium.

3. The catalyst system as claimed in claim 1, wherein the metal complex and the organic compound having a cyclic structure containing at least one double bond have a molar ratio of 0.1:1-50:1.

4. The catalyst system as claimed in claim 1, wherein the organic lithium compound and the metal complex have a molar ratio of 1:1-12:1.

5. The catalyst system as claimed in claim 1, wherein the organic compound having a cyclic structure containing at least one double bond and the organic lithium compound have a molar ratio of 0.1:1-12:1.

* * * * *